(12) United States Patent
Ovokaitys et al.

(10) Patent No.: US 8,404,733 B2
(45) Date of Patent: Mar. 26, 2013

(54) LASER ENHANCED AMINO ACID BLEND AND USE OF SAME TO REGENERATE ACTIVE MYOCARDIAL TISSUE

(75) Inventors: Todd F. Ovokaitys, Carlsbad, CA (US); Vladimir S. Fedorov, Izhevsk (RU)

(73) Assignee: Todd F. Ovokaitys, Carlsbad, CA (US)

( * ) Notice: Subject to any disclaimer, the term of this patent is extended or adjusted under 35 U.S.C. 154(b) by 0 days.

(21) Appl. No.: 13/026,454

(22) Filed: Feb. 14, 2011

(65) Prior Publication Data

US 2012/0220641 A1  Aug. 30, 2012

Related U.S. Application Data

(60) Provisional application No. 61/337,951, filed on Feb. 12, 2010.

(51) Int. Cl.
*A61K 31/415* (2006.01)
*A61K 31/195* (2006.01)

(52) U.S. Cl. ......... 514/400; 514/561; 514/562; 514/565

(58) Field of Classification Search .................. 514/400, 514/561, 562, 565
See application file for complete search history.

(56) References Cited

U.S. PATENT DOCUMENTS

| 5,571,797 A | 11/1996 | Ohno et al. |
| 6,064,500 A | 5/2000 | Strachan |
| 6,811,564 B1 | 11/2004 | Strachan |
| 2002/0058952 A1 | 5/2002 | Weber et al. |
| 2004/0204746 A1 | 10/2004 | Ovokaitys et al. |
| 2008/0183162 A1 | 7/2008 | Altshuler et al. |

FOREIGN PATENT DOCUMENTS

WO  2008/013985  1/2008

OTHER PUBLICATIONS

International Search Report of PCT/US11/024694, dated Apr. 25, 2011.
International Preliminary Report on Patentability and Written Opinion of the International Search Report of PCT/US11/024694, dated Aug. 23, 2012.

*Primary Examiner* — Raymond Henley, III
(74) *Attorney, Agent, or Firm* — Kenyon & Kenyon LLP

(57) ABSTRACT

The invention provides a blend of amino acid powders that have been exposed to pulsed laser radiation. The pulsed laser radiation is obtained by passing laser radiation through a device, which has a first diffraction grating, a second diffraction grating, and a refractive element positioned between the first and second diffraction gratings. Passing the laser radiation through the device cancels a portion of the laser radiation by destructive interference, and produces pulses of laser radiation by constructive interference. The blend of laser treated amino acids has been found useful in regenerating active myocardial tissue. The invention further provides a process for preparing the laser treated blend of amino acid powders and a method of regenerating active myocardial tissue with the blend.

18 Claims, 3 Drawing Sheets

Before Treatment

After Treatment

LASER ENHANCED AMINO ACID BLEND AND USE OF SAME TO REGENERATE ACTIVE MYOCARDIAL TISSUE

RELATED APPLICATION

This application claims benefit of U.S. Provisional Patent Application No. 61/337,951, filed Feb. 12, 2010, the contents of which are incorporated herein in their entirely by reference.

BACKGROUND

Congestive heart failure (CHF) is a common problem worldwide, affecting approximately 5 million people in the U.S. alone. Many pathologic conditions can reduce the pump function of the heart, the most common being ischemic heart disease and hypertension. While the clinical symptoms of the failing myocardium improve with conventional treatment with agents such as vasodilators, diuretics, and inotropic compounds, such treatment does little to repair the underlying myocardial pump weakness.

Any method and/or composition that regenerates active myocardial tissue would be expected to improve the condition of persons with congestive heart failure. The present invention provides such a method and composition.

SUMMARY OF THE INVENTION

Amino acids are the core building blocks of all proteins, myocardial and otherwise. The present invention improves myocardial structure and function with a broad spectrum blend of protein synthetic amino acids. Treated patients show a marked improvement in clinical signs and symptoms, a significant reduction in cardiac arrhythmias, and marked functional and structural improvement of the myocardium, all of which beneficial changes were statistically significant. In sharp contrast, control subjects taking a placebo had no improvement or a worsening of all those cardiovascular related parameters. While some amino acids have shown favorable effects on heart function at high doses, the relatively low doses of individual compounds of the present invention provide a profoundly beneficial effect for heart failure that greatly exceeded any a priori expectations of the sum of effects of individual compounds.

The present invention provides a blend of amino acids that, upon effective delivery to the body, reverses the symptoms, signs, electrical instability, and abnormal physiology and hemodynamics of congestive heart failure. Preferably, the blend of amino acids has been enhanced in activity with a laser. Preferably, the dosage of the blend is at least about 2 grams, 3 times per day, and, more preferably, about 2 grams, 3 times per day.

A blend of amino acids of the invention, upon effective delivery to the body, stimulates the regeneration of functional myocardium. Preferably, the blend has been enhanced in activity with a laser that, upon effective delivery of the enhanced blend to the body stimulates the regeneration of functional myocardium.

In accordance with the invention, the blend of amino acids comprises a plurality of amino acid powders exposed to pulsed laser radiation. The pulsed laser radiation is obtained by passing laser radiation through a device comprising a first diffraction grating, a second diffraction grating, and a refractive element positioned between the first and second diffraction gratings. When laser radiation is passed through such a device, a portion of the laser radiation is canceled by destructive interference, and pulses of laser radiation are produced by constructive interference. Preferably, the pulsed laser radiation has a pulse length of no more than $10^{-9}$ seconds. Useful results have been obtained with a laser having a center frequency of about 400 to about 550 nm.

The invention further provides a process for preparing a laser treated blend of amino acids. The process comprises obtaining a blend of amino acid powders; and exposing the blend of amino acids to pulsed laser radiation from the device described above The invention further provides a method of regenerating active myocardial tissue. The method comprises comprising administering a blend of amino acids, comprising a plurality of amino acid powders exposed to pulsed laser radiation, to a patient, where the pulsed laser radiation obtained by passing laser radiation through the device described above.

DETAILED DESCRIPTION OF THE PREFERRED EMBODIMENTS

Figure 1:
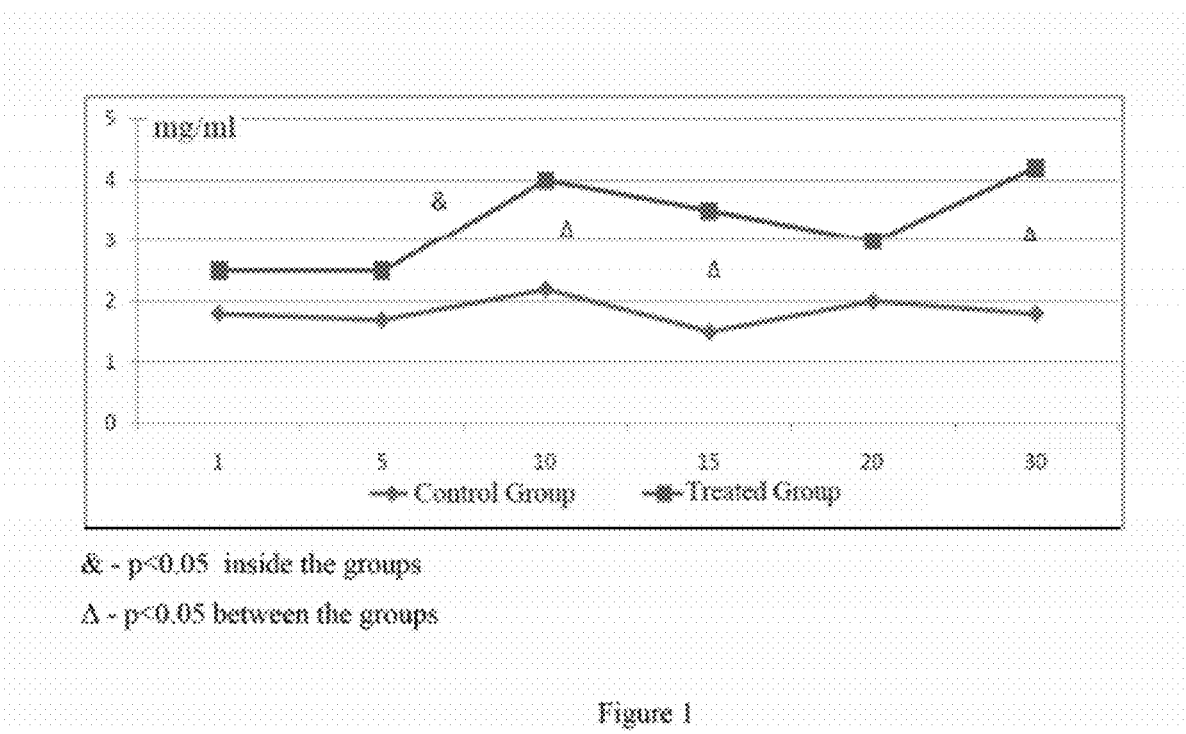
FIG. 1 illustrates the dynamics of PCO content for patients in treated and control groups.

The present invention is directed to a blend of amino acids subjected to laser radiation for the regeneration of myocardial tissue, a method of preparing such a blend of amino acids, and a method for the regeneration of myocardial tissue by administration of the amino acid blend.

The amino acid blends of the invention are prepared by blending a mixture of amino acids powders, and exposing the powder blend to of laser light from at one or more laser sources. Where more than one laser source is used, the lasers are of different wavelengths, and may be applied simultaneously or in alternating sequences.

The blend of amino acid powders is typically a blend of the amino acids found in the proteins of myocardial tissue. Preferably, the amino acid blend is a blend of glycine, DL-phenylalanine, L-glutamic acid, L-lysine, L-glutamine, L-arginine, L-leucine, L-isoleucine, L-valine, L-methionine, L-serine, L-threonine, L-alanine, L-aspartic acid, L-histidine, L-proline, L-ornithine, L-citrulline, L-taurine, and L-cysteine.

More preferably, the amino acid blend is a blend of 34.1±3.4 percent by weight glycine, 11.9±1.19 percent by weight DL-phenylalanine, 6.3±0.63 percent by weight L-glutamic acid, 6.3±0.63 percent by weight L-lysine, 6.3±0.63 percent by weight L-glutamine, 5.6±0.56 percent by weight L-arginine, 5.6±0.56 percent by weight L-leucine, 3.7±0.37 percent by weight L-isoleucine, 3.1±0.31 percent by weight L-valine, 3.1±0.31 percent by weight L-methionine, 3.1±0.31 percent by weight L-serine, 2.5±0.25 percent by weight L-threonine, 1.6±0.16 percent by weight L-alanine, 1.3±0.13 percent by weight L-aspartic acid, 1.3±0.13 percent by weight L-histidine, 1.3±0.13 percent by weight L-proline, 1.1±0.011 percent by weight L-ornithine, 0.9±0.09 percent by weight L-citrulline, 0.6±0.06 percent by weight L-taurine, and 0.3±0.03 percent by weight L-cysteine.

Particularly useful results have been obtained with an amino acid blend of about 34.1 percent by weight glycine, 11.9 percent by weight DL-phenylalanine, 6.3 percent by weight L-glutamic acid, 6.3 percent by weight L-lysine, 6.3 percent by weight L-glutamine, 5.6 percent by weight L-arginine, 5.6 percent by weight L-leucine, 3.7 percent by weight L-isoleucine, 3.1 percent by weight L-valine, 3.1 percent by weight L-methionine, 3.1 percent by weight L-serine, 2.5 percent by weight L-threonine, 1.6 percent by weight L-alanine, 1.3 percent by weight L-aspartic acid, 1.3 percent by weight L-histidine, 1.3 percent by weight L-proline, 1.1 percent by weight L-ornithine, 0.9 percent by weight L-citrulline, 0.6 percent by weight L-taurine, and 0.3 percent by weight L-cysteine.

Preferably, the laser radiation is pulsed at a relatively high pulse repetition rate, having an effective pulse length no greater than the picosecond range, i.e., $10^{-12}$ to $10^{-9}$ second, and may be in the femtosecond range, i.e., $10^{-15}$ to $10^{-12}$ second, or the sub-femtosecond range, i.e., $<10^{-15}$ second. Where a single laser source is used, the laser preferably has an emission centered in the lower half of the visible spectrum, i.e., between about 400 and about 550 nm, preferably, in the near ultraviolet (UV) to blue range, more preferably, at a wavelength from about 400 to about 470 nm.

Where a second laser is used, the second laser preferably has an emission centered in the upper half of the visible spectrum, i.e., between about 550 and about 700 nm, preferably, in the red to near infrared (IR), more preferably at a wavelength of from about 620 to about 680 nm. Using two lasers having emissions centered at similar wavelengths, i.e., two short wavelength lasers, two long wavelength lasers, or two lasers with emissions centered near 550 nm, may be useful in some applications. However, good results have been obtained with a single laser having a center wavelength of from about 400 to about 470 nm. Lasers having a center wavelength of 405 and 458 nm has been found to be particularly useful.

Without being bound by theory, it is believed that the output bandwidth of the lasers is broadened by the short effective pulse length. That follows from the Uncertainty Principle. As a result, the short pulses of laser light are believed to provide photons that interact with multiple vibrational and/or electronic states in the process of the invention. As a result, lasers having emissions that correspond to specific absorption bands of the treated blend of amino acids are not required.

Preferably, the ultra-short laser pulses are produced by modifying the output of the lasers to generate sparse nodes of constructive interference of electromagnetic (EM) waves, as disclosed by U.S. Pat. Nos. 6,064,500 and 6,811,564 to Strachan, the disclosures of which are incorporated herein in their entirety by reference. The device used to produce the pulsed laser radiation, as defined in the '500 and '564 patents, and as used herein, comprises a first diffraction grating and a second diffraction grating and a refractive element positioned between the first and second diffraction gratings.

When a laser beam, either continuous or pulsed, is passed sequentially through the first diffraction grating, the refractive element, and the second diffraction grating of a such a device, at least a portion of the beam is substantially canceled by destructive interference. The interaction of light beams that pass through the device results in destructive interference that substantially cancels the beams as they exit the device. The refractive element allows the cancellation to occur over a small percentage of the laser source rather than at a single critical wavelength.

Relatively sparse zones of constructive interference occur between the high and low frequency passes of the cancellation element in selected directions from the aperture. The sparse nodes of constructive interference occur only where the output of the device results in constructive interference at a distance from the device. The constructive interference only occurs over ultra-short time periods, and, thus, results in ultra-short pulses of light. The pulses are believed to have effective pulse lengths of no more than about $10^{-9}$ seconds.

With a the device used in the present invention for producing pulsed laser radiation, fractional changes in the wavelength of the laser or relative amplitudes of wavelengths in the laser cause rapid translation in the location of these nodes, as, for example, fractional changes in current in a laser diode and fluctuations in junction temperature causing variations in the laser center frequency. As a result, a continuous laser beam is transformed into a string of extremely short duration pulses by the simple means of relatively small low frequency amplitude modulation. The amplitude modulation of diode lasers at a frequency of over 1 MHz is well within the skill of those skilled in the art. As a result, effective pulse lengths having a duration in the picosecond range are readily attainable, and femtosecond or sub-femtosecond pulses are attainable with a properly prepared device and amplitude modulated diode laser.

For example, with a continuous diode laser, the pulse repetition frequency of the string of extremely short duration pulses is defined by the amplitude modulation frequency of the direct laser diode drive or the acousto-optic or electro-optic modulation device. The inherent current modulation of the direct laser drive method will result in more fluctuation in laser center frequency reducing the period of the coincident pulses while acousto-optic modulation provides a similar effect if the aperture of the modulated beam is greater than the diameter of the optimal modulation aperture of the crystal, as the outer radii will be less deeply modulated than the inner radii causing the effective aperture in the function to alter.

In the present method of producing the laser modified blend of amino acids, a rapid sequence of ultra-short laser pulses from at least one laser is applied to a blend of amino acid powders. As discussed above, it is believed that the output bandwidth of the lasers is broadened by the short pulse length. Again, that follows from the Uncertainty Principle. As a result, the short pulses of laser light are believed to provide photons that interact with multiple vibrational and/or electronic states of the composition to provide the laser modified blend of amino acid powders. As a result, lasers having an emission that corresponds to a specific absorption band of the composition are not required, and, thus, the choice of lasers is not critical. Good results have been obtained with a diode laser that emits in the blue-violet band, preferably about 400 to about 470 nm, and, most preferably, about 405 nm. Good results have also been obtained with 458 nm laser radiation obtained from a pumped argon gas laser.

Preferably, the sequence of laser pulses comprises sparse nodes of constructive interference of ultra short duration in the wavelength region produced by the laser and a device for modulating the laser radiation, as described above. Without being bound by theory, it is believed that the sequence of ultra-short laser pulses interacts with the electronic and/or vibrational states of the molecules of the composition.

Although the process of the invention has been shown to provide useful laser treated amino acid blends when the amino acids are exposed to laser radiation in the presence of normal air, the process may also be performed in an inert atmosphere. The inert atmosphere may be provided using nitrogen, helium, argon, or other inert gas. For cost reasons, nitrogen is preferred. The use of the inert gas will eliminate any tendency of oxidation during the process. It will be clear to those skilled in the art that the best results are obtained when the depth of the blend of amino acids exposed to the laser radiation is such that the laser radiation penetrates through the entire sample, exposing the entire amino acid powder blend to the laser radiation.

Laser treated amino acid blends can be used for the regeneration of myocardial tissue, preferably in a treatment of congestive heart failure. Dosage will be determined based on the weight of the individual treated and the amount of myocardial tissue that requires regeneration. Preferably, multiple doses will be administered each day. For example, about 1 to about 3 grams of a laser treated blend of amino acid powders can be administered about 4 to about 5 times per day. More preferably, about 2 grams of a laser treated blend of amino acid powders is administered 3 times per day.

EXAMPLES

An in vitro study and a clinical study were performed to test the compositions and method of the invention. The amino acid complex metabolic formulation used in the clinical study contains the following free form amino acids in the indicated ratios: glycine (34.1 percent), DL-phenylalanine (11.9 percent), L-glutamic acid (6.3 percent), L-lysine (6.3 percent), L-glutamine (6.3 percent), L-arginine (5.6 percent), L-leucine (5.6 percent), L-isoleucine (3.7 percent), L-valine (3.1 percent), L-methionine (3.1 percent), L-serine (3.1 percent), L-threonine (2.5 percent), L-alanine (1.6 percent), L-aspartic acid (1.3 percent), L-histidine (1.3 percent), L-proline (1.3 percent), L-ornithine (1.1 percent), L-citrulline (0.9 percent), L-taurine (0.6 percent), and L-cysteine (0.3 percent).

This composition was treated with laser radiation after the method of Strachan described in U.S. Pat. No. 6,811,564 to enhance bioavailability of the compounds. As discussed above, the laser radiation was obtained by passing laser radiation through a device comprising a first diffraction grating, a second diffraction grating, and a refractive element positioned between the first and second diffraction gratings, thereby canceling a portion of the laser radiation by destructive interference, and producing pulses of laser radiation by constructive interference.

The powder was treated with a beam of 405 nm wavelength, at about 40 percent beam energy phase cancellation after passage through the device (creating non-fringing destructive interference combined with sparse nodes of constructive interference) to deliver about 1 mW per kilogram per minute.

The rationale for the use of this process of laser enhancement is the result of an in vitro study using a similar short wavelength laser treatment. In this study, murine macrophages that were activated with Echinacea to simulate an irritated immune system were then fed the above formula of amino acids in the untreated and laser treated conditions. Untreated amino acids resulted in a marked pro-inflammatory response as demonstrated by a highly significant approximately 2.3 fold increase in tumor necrosis factor-alpha (TNF-alpha), a known major mediator of the inflammatory process. In contrast, feeding the treated amino acids to the Echinacea activated macrophages resulted in no greater inflammatory response than that produced just by the Echinacea stimulation.

The specific details of the in vitro study are as follows. 20 grams of the amino acid blend as detailed above was used for each of the control and treated amino acid samples. The Untreated Sample was not treated. The Treated Sample was exposed to laser radiation from a 458 nm pumped argon gas laser with a primary power of 16.5 mW adjusted through the optics to a power level of 5.1 mW The duration of treatment of the sample was 30 seconds.

The following bioassays were performed. A standardized Echinacea sample alone or with 20 mg/ml of the Untreated or Treated Sample amino acids were incubated in tissue culture media of triplicate wells of murine macrophages. After 24 hours of Echinacea stimulation, the macrophages treated under the various conditions were assayed for TNF-alpha production in triplicate enzyme-linked immunosorbent assay (ELISA) wells. Positive Controls with lipopolysaccharide (LPS) at 1 ng/ml and Negative Controls without Echinacea, LPS, or amino acid stimulation were assayed in the same manner.

Those skilled in the art will appreciate that the use of murine macrophages simulates the human body's immune response. Adding the herb Echinacea provides a similar response to that of an immune system that is being irritated. TNF-alpha is a relevant marker for identifying the extent of inflammation being induced in response to an irritating stimulus. Thus a substance that causes a significant increase in TNF-alpha in the macrophages can be expected to create substantial inflammation in the human body, or a modifying factor that reduces TNF-alpha would be expected to reduce the inflammatory response in the body.

The results were as follows and are expressed as the mean TNF-alpha production plus or minus the statistical standard deviation (SD):

| Sample ID | TNF-alpha +/− SD | p* |
|---|---|---|
| Negative Control | 215 +/− 13.7 | |
| LPS 1 ng/ml Positive Control | 2863 +/− 185.7 | |
| *Echinacea* Stimulated Sample | 683 +/− 27.1 | — |
| *Echinacea* + Untreated Amino Acid Sample | 1568 +/− 45.8 | <.0001 |
| *Echinacea* + Treated Amino Acid Sample | 761 +/− 100.3 | .31 |

*p value compared to *Echinacea* Stimulated Sample

Using a Student's 2-tailed t-test, the Echinacea Stimulated Sample was compared to the results of Echinacea plus the Untreated Amino Acid Sample or the Treated Amino Acid Sample. The addition of the Untreated Amino Acid Sample resulted in a highly statistically significant 2.3-fold increase in TNF-alpha, with p<0.0001. The addition of the Treated Amino Acid Sample did not significantly increase TNF-alpha production, with p=0.31. Expressed alternatively, the laser treated amino acids resulted in an approximately 11-fold reduction of the pro-inflammatory effect of the untreated amino acids, essentially to that of adding Echinacea only.

Without being bound by theory, the results of this in vitro study suggest that untreated amino acids may aggravate an inflammatory process that is already present, whereas the treated amino acids will not aggravate inflammation and can still serve as basic repair nutrients. The implication is that the treated amino acids may produce a better physiologic result in the treatment of heart failure because untreated amino acids may aggravate the inflammatory process that may already be present, whereas the treated amino acids will not aggravate inflammation while also actively supporting the myocardial repair activities.

The dosage of the study formula used was 3 gelatin capsules of about 667 mg each three times per day, for a total dose of 6.0 grams daily. All the amino acids used were well within safe levels known for these widely consumed compounds.

Fifty subjects were selected for the study, all with both hypertension and cardiac ischemia complicated by a range of severity of congestive heart failure. The subjects were stratified by severity of heart failure, with 30 subjects randomly assigned to the treatment group and 20 subjects assigned to the placebo control group. Clinical and lab studies were done at baseline and after 30 days of the program. Comparative data were felt to be statistically significant if a p value of 0.05 or less was achieved. The protocol was reviewed and approved by the Ethics Committee of the Izhevsk State Medical Academy. Informed consent was received from all study participants.

The work was carried out in the "Doctor" Clinic of Natural Medicine (Izhevsk) by the employees of the Izhevsk State Medical Academy in a number of leading clinics of the Udmurt Republic and in the hospital therapy faculty of the Izhevsk State Medical Academy.

Main Tasks of the Study

Assessment of course intake influence of the amino acid complex metabolic formulation on the clinical disease course of the patients suffering from various degree of circulatory inefficiency Assessment of dynamics of the amino acid complex metabolic formulation on myocardial contractile force according to echocardiography data Assessment of the amino acid complex metabolic formulation action on parameters of biopolymer exchange according to oxyproline exchange data The analysis of the amino acid complex metabolic formulation action was carried out on the basis of:
  Clinical data
  Biochemical markers
  Instrumental methods of study Clinical Data Several clinical symptoms and signs of disease, such as asthenia, dyspnea, and acrocyanosis were assessed depending on the degree of manifestation of a clinical symptom or sign according to 4-score system, where
  0—no symptom or sign
  1—mild symptom or sign
  2—moderate symptom or sign
  3—severe symptom or sign expression
Some objective parameters were summarized in the form of tables, drawings, or schedules.

Laboratory Data

The level of metabolic process intensity in connective tissue of myocardial stroma was defined by means of peptide bound oxyproline. Oxyproline is an amino acid formed during collagen biosynthesis when proline is oxidized. Oxyproline content was analyzed with the help of P. N. Sharaev's modified method (1981) in the biochemistry faculty of the Izhevsk State Medical Academy.

Instrumental Data

Cardiac echocardiography was made by means of the ultrasonic diagnostic technology known as "Zonar" (USA). The systolic function of the left ventricle was assessed by measurement of the left ventricular ejection fraction (LVEF), the normal value being 50 to 65 percent. End-diastolic and end-systolic dimensions of the left ventricle were defined in M conditions, and end-diastolic and end-systolic volumes of the left ventricle were defined by bidimensional analysis. Depending on the severity of systolic dysfunction, all patients were divided into 3 groups:

Group 1 with mild decrease of contractility, LVEF 40-50 percent

Group 2 with moderate decrease of contractility, LVEF 30-40 percent

Group 3 with severe decrease of contractility, LVEF <30 percent

Left ventricular diastolic function was also assessed according to the rate of early diastolic filling. Increase of the early diastolic filling to a value of more than 220 ms (the norm is 73±24 ms) indicates appreciable diastolic dysfunction of the left ventricle and reflects pressure increase of left ventricle filling (V. V. Mitkova, V. A. Sandrakova, 1998).

Statistical Processing of the Data

Statistical processing of the data was made with the standard software package MS Excel 2003 for small sampling according to the Student and Fisher methods with probability assessment at the $p<0.05$ and $p<0.01$ levels. The present report indicates the average value "±" the standard error of the analysis.

Characteristics of the Study Population

Fifty patients were included into the clinical, biochemical, and instrumental studies. 30 patients were treated with the amino acid complex metabolic formulation. Average age of patients from this group was 50.3±2.5, of which 24 were males and 6 females. In the control group (n=20) there were 16 males and 4 females taking part in the study. The average age of the patients from the control group was 56.3±3.2. There were no significant differences in age or gender ratio between the treated and control groups.

The clinical characteristics according to the severity and clinical signs of disease are presented in Table 1.

TABLE 1

Clinical characteristics of patients from treated and control groups

| Parameter | Treated group, n = 30 | Control group, n = 20 |
|---|---|---|
| Hypertension | 30 | 20 |
| CHD | 30 | 20 |
| Congestive Heart Failure | 30 | 20 |
| Stage 1 | 8 | 4 |
| Stage 2 | 12 | 9 |
| Stage 3 | 10 | 7 |
| Rhythm disturbance, solely extrasystoles | 22 | 16 |
| Atrial Fibrillation | 4 | 2 |
| Cardiostimulator | 2 | — |
| Stroke consequences | 4 | 1 |
| Valvular defect | 2 | — |

Treated and control groups did not differ from each other regarding the overall clinical features or the stratification of severity of clinical features.

The clinical symptoms of disease and relative severity of selected symptoms are presented in Table 2.

TABLE 2

Intensity of clinical symptoms and signs of patients from treated and control groups

| Disease symptom | Treated group, n = 30 | Control group n = 20 |
|---|---|---|
| Weakness | 23 | 14 |
| Headache | 26 | 16 |
| Sense of air lack (dyspnea) | | |
| at load | 28 | 16 |
| at rest | 2 | 4 |
| Pressing pain under breast bone | 26 | 16 |
| Acrocyanosis: | | |
| mild | 6 | 6 |
| moderate | 8 | 8 |
| severe | 16 | 12 |
| Stagnation at lesser circulation | 12 | 8 |
| Edema of lower extremities | | |
| mild | 6 | 5 |
| moderate | 16 | 8 |
| severe | 8 | 7 |
| Rhythm disturbance: | | |
| ventricular | 12 | 9 |
| supraventricular | 23 | 5 |
| Chronic Atrial Fibrillation | 11 | 6 |

Treated and control groups did not differ from each other regarding the overall clinical symptoms or the stratification of severity of clinical symptoms. Thus, for patient demographics, clinical symptoms, and clinical signs treated and control groups were well matched, with no statistically significant differences for any of the measured characteristics.

All patients were taking conventional medical therapy targeting optimum control of heart failure and related symptoms and signs. The following groups of medicines were among those applied during treatment to achieve clinical control of the subjects' condition: ACE inhibitors, diuretics, cardiac glycosides, anti-arrhythmic drugs, and nitrates. Metabolic therapy other than use of the study formula in the treated group was not applied in the treatment.

Before the course of the amino acid complex metabolic study formulation or placebo was given, all patients underwent baseline history and physical examinations, as well as lab testing including relevant biochemical markers, echocardiography, and Holter monitoring. After completing the 30 day course of the amino acid complex or placebo, the clinical and laboratory exams were repeated.

The results of baseline and follow-up clinical examinations are given in Table 3.

Examination Results

TABLE 3

Comparative levels and intensities of clinical symptoms for patients in treated versus control groups before and after 30 days

| Name of disease symptom | Main group | | Reference group | |
|---|---|---|---|---|
| | Before treatment | After 30 days | Before treatment | After 30 days |
| Subjective symptoms | | | | |
| Weakness | 59 ± 8(23) | 20 ± 7(3)* | 70 ± 10(14) | 65 ± 11(13) |
| Headache | 67 ± 8(26) | 44 ± 9(13) | 65 ± 11(16) | 35 ± 11(17)* |
| Shortness of breath | | | | |
| at load | 93 ± 5(28) | 17 ± 7(5)* | 80 ± 9(16) | 65 ± 11(13) |
| at rest | 7 ± 5(2) | 0* | 20 ± 9(4) | 20 ± 9(4) |
| Pressing pain under breast bone | 87 ± 6(26) | 70 ± 9(21) | 65 ± 11(16) | 50 ± 12(10) |
| Objective symptoms Acrocyanosis | | | | |
| Mild | 20 ± 7(6) | 0* | 32 ± 11(6) | 25 ± 10(5) |
| Moderate | 27 ± 8(8) | 0* | 42 ± 12(8) | 42 ± 12(8) |
| Severe | 53 ± 9(16) | 20 ± 7(6)* | 60 ± 11(12) | 50 ± 12(10) |
| Stagnation at lesser circulation | 40 ± 9(12) | 7 ± 5(2)* | 42 ± 12(8) | 35 ± 11(6) |
| Edemas at lower Extremities | | | | |
| Mild | 20 ± 7(6) | 0 ± 3(0) | 25 ± 10(5) | 20 ± 9(4) |
| Moderate | 53 ± 9(16) | 9 ± 3(2) | 40 ± 11(8) | 30 ± 10(6) |
| Severe | 27 ± 8(8) | 0 ± 3(0) | 35 ± 11(7) | 35 ± 11(7) |
| no edema | — | — | — | — |
| Rhythm disturbance | | | | |
| Ventricular | 40 ± 9(12) | 7 ± 5(3)* | 45 ± 11(9) | 80 ± 9(1 5)* |
| Supraventricular | 76 ± 8(23) | 40 ± 9(12)* | 25 ± 1(5) | 45 ± 11(9)* |
| Atrial fib | 37 ± 9(11) | 30 ± 9(9) | 30 ± 10(6) | 30 ± 10(6) |

*p < .0

Results of clinical histories and physical examinations show a statistically significant positive action of the use of the amino acid complex metabolic formulation on improving the symptoms and signs of congestive heart failure in the treated compared to the placebo control group. Subjective symptoms and objective signs that were improved include the following: statistically significant reduction of weakness, decreased shortness of breath at rest and with exertion, as well as reduction of acrocyanosis. In addition, the presence and degree of peripheral edema for patients in the treated group was much improved. In contrast, there was no improvement in these heart failure related symptoms in the placebo control group.

Improvement of the condition of the treated subjects was accompanied by statistically significant reduction of the quantity of supraventricular and ventricular arrhythmias detected during patients' examination, during 12-lead ECG examination, and during 24 hour Holter monitoring for arrhythmias (p<0.05). It is especially notable that ventricular arrhythmias, a life threatening complication of heart failure, resolved for the majority of subjects taking the amino acid complex, their prevalence reduced from 40 percent to 7 percent of the treated subjects. In contrast, the subjects in the placebo control group showed a significant increase in the frequency of ventricular and supraventricular arrhythmias (p<0.05), with ventricular arrhythmias increased from 45 percent to 80 percent of the untreated control group.

The prevalence of chronic atrial fibrillation was reduced but not to a significant degree in the treated group. There was no change in the prevalence of this arrhythmia in the placebo group.

Thus the intake of the amino acid complex for congestive heart failure was associated with significant improvement of clinical symptoms and signs, enhanced quality of life, and stabilization of electrical activity of the heart as demonstrated by reduction of arrhythmias. In comparison the placebo control group showed no improvement or worsening of clinical symptoms and signs, and particularly showed an increase in life endangering ventricular arrhythmias.

Laboratory Examination Methods

Determination of the metabolic activity of amino acid biopolymers before and after the intake of the amino acid complex was studied by measuring for changes in oxyproline (PCO) levels, which is illustrated in FIG. 1. The mechanism of action of oxyproline change is directly connected with phospholipid synthesis and shifts of RNA and ATP in the cells of myocardial connective tissues that are involved in myocardial energetic and regeneration processes. We measured the effect of taking the activated amino acid complex on PCO levels in treated versus placebo groups, with changes in PCO levels reflecting differential synthesis of myocardial collagen and alterations of energetic support of cardiac muscle.

Initial PCO levels for patients in the treated group, 2.32±0.6 μg/ml, and the control group, 1.95±1.8 μg/ml, did not differ from each other ($p>0.1$). Further PCO dynamics in the treated group was notable for a rise of oxyproline from the $5^{th}$-$7^{th}$ day of intake of the activated amino acid complex reflecting synthesis of new collagen. Further, the PCO dynamics during the intake of the amino acid complex bioactive substance demonstrates a higher level ($p<0.05$) of increased collagen production during the whole course of bioactive substance intake. The PCO level increased to 3.8±0/3 μg/ml at the end of the second week, and it achieved a level of 4.2±0.5 μg/ml at the end of 30-day course.

The PCO levels did not change significantly in the control group, and the levels remained significantly lower than those of the treated group during the whole month of observation. Thus the intake of the amino acid complex caused intensification of beneficial energetic and regenerative myocardial metabolic process for patients with cardiac decompensation. The increased use of amino acids for protein synthesis in myocardial stroma coincided in time with improved clinical conditions of the patients at the second week of intake of the bioactive substance.

Results of echocardiography of patients from the treated and control groups

Figure 2A:
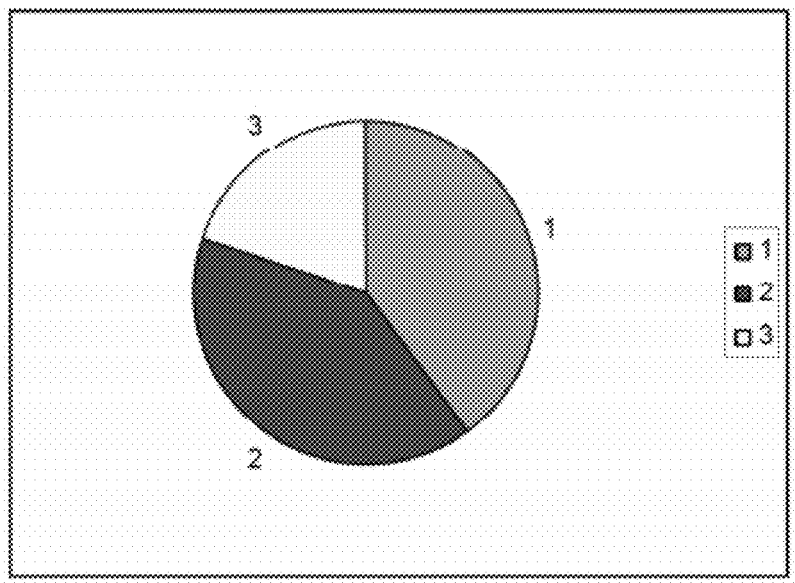
FIG. 2 illustrates relative degrees of systolic dysfunction for the treated group at baseline (2A) and after 30 days of treatment with the bioactive substance of the invention (2B).

Ultrasonic cardiography, also known as echocardiography, was conducted with 19 patients from the treated group and with 14 patients from placebo group at baseline and after 30 days. Patients with chronic atrial fibrillation were excluded from the testing due to difficulty of analysis caused by the highly variable degrees of ventricular filling in this condition. Depending on the degree of systolic dysfunction of the left ventricle (LV), patients were divided into three groups: group 1 patients with an ejection fraction (EF) of 40 to 50 percent; group 2 patients with an ejection fraction 30-40 percent and group 3 patients with ejection fractions of <30 percent (V. V. Mitkov, V. A. Sandrikova, 1998). LVEF between 40 to 50 percent was determined in 42±12 percent of patients. Moderate systolic dysfunction with LVEF between 30-40 percent was determined also for 42±12 percent, and severe systolic dysfunction with LVEF <30 percent was determined in 21±10 percent of the treated cases. The initial results before using the amino acid complex capsules are shown in the FIG. 2A.

Figure 2B:
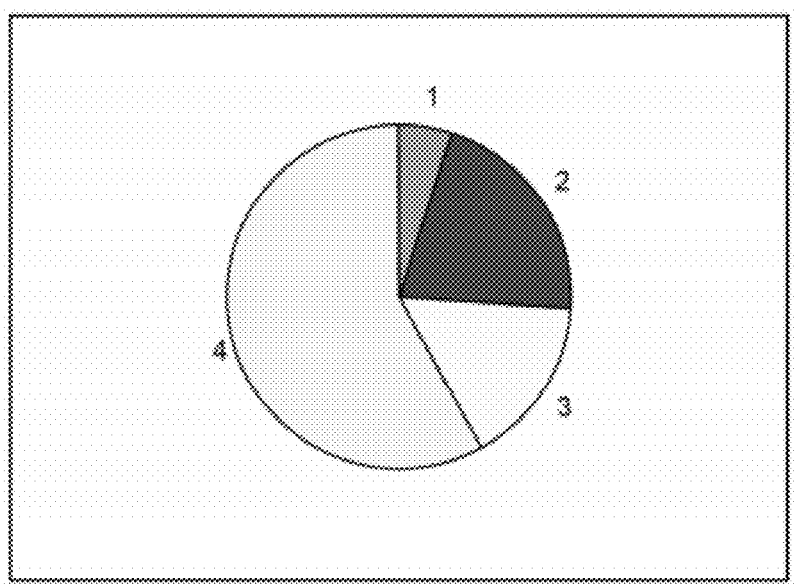

Following 30 days of use of the amino acid complex formula, the ultrasonic cardiography was repeated. The results are shown in FIG. 2B. Beyond all pre-study expectations, the systolic function of 58±8 percent of the patients improved to normal or nearly normal. Clinically these patients had resolution of edema of the lower extremities and marked improvement of shortness of breath, especially of exertional dyspnea. These changes took place largely due to improvement in group 1 patients, which improved from 42±12 percent to 5±5 percent of the treated population. Nevertheless, the indices of patients from group 2 also improved significantly from 42±12 percent to 21±10 percent ($p<0.05$) of the treated group. Even the most severely ill patients from group 3 with LVEF <30 percent experienced improvement of systolic function, with a reduction from 21±10 percent to 16±9 percent of the group; however, the relatively small number of subjects in this category makes this subgroup analysis statistically inconclusive.

Figure 3A:
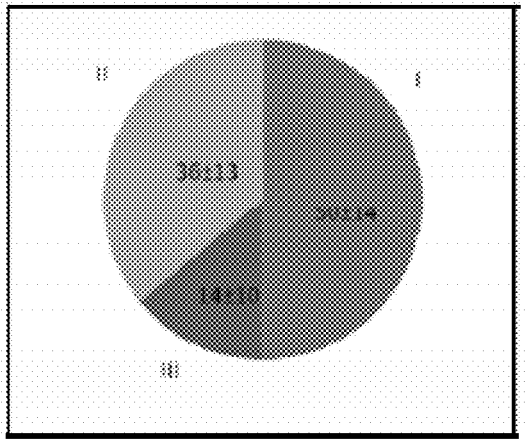
FIG. 3 illustrates relative degrees of systolic dysfunction for the control group at baseline (3A) and after 30 days of use of the placebo (3B).
Figure 3B:
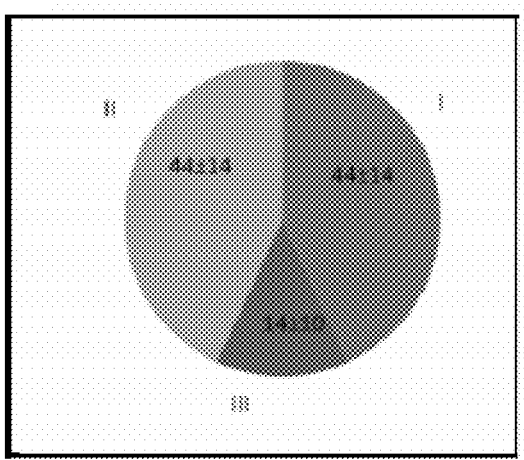

The group stratification of the patients from placebo group at baseline and after the 30 days of the study is shown in FIG. 3. Echocardiographic indices of systolic dysfunction of the LV showed no significant changes over the 30 days of the study.

Table 4 shows the time course of cardiac circulatory dynamics with data generated via ultrasonic cardiography (Zonar) of patients from the treated and placebo control groups at baseline and after 30 days. Table 4 shows the average values and variability for the LV ejection fraction as well as end-systolic volume, end-diastolic volume, and end-systolic and end-diastolic dimensions of the left ventricle. The treatment group showed statistically significant improvement of all of these parameters. In contrast, none of these values showed a significant change for the placebo control group.

Table 4 also shows an analysis of the time course of diastolic function of the LV. Improvement of this temporal parameter towards normal suggests a decrease of ventricular filling pressure and improved contractile function of the myocardium. This value was statistically significantly improved towards normal in the treatment group and essentially unchanged in the placebo control group.

TABLE 4

Cardiac Ultrasound (Zonar) derived indices of cardiac dynamics of patients from the treated and placebo control groups at baseline and after 30 days
Index M = m volume

| Index | Basic group | | Test group | |
|---|---|---|---|---|
| | Before treatment | In 30 days | Before treatment | In 30 days |
| EF (ejection fraction), % | 36.2 ± 2.1 | 44.9 ± 1.8* | 37.9 ± 2.8 | 34.3 ± 2.6 |
| ESV(end-systolic volume), ml | 107.3 ± 4.9 | 81.2 ± 3.28* | 98.4 ± 4.2 | 105.2 ± 4.2 |
| EDV (end-diastolic volume), ml | 168.2 ± 6.2 | 147.3 ± 4.9* | 158.6 ± 3.0 | 160.3 ± 3.2 |
| ESD(end-systolic dimension), ml | 67.2 ± 2.3 | 60.8 ± 4.2* | 69 ± 1.6 | 63 ± 4.1 |
| EDD(end-diastolic dimension), ml | 53.1 ± .8 | 44.6 ± 1.6* | 56 ± 2.1 | 51 ± 3.2 |
| Dynamics of diastolic function (msec) | 148 ± 6.3 | 111 ± 4.5* | 138 ± 4.8 | 142 ± 5.2 |

*p < .05

Thus, the aggregate indices of systolic and diastolic function indicate a highly significant improvement of contractile function of left ventricle as a result of the course of treatment with the amino acid complex metabolic formulation. The profundity of the improvement is indicated by the marked reshaping of the dilated and failing hearts of the treated subjects to nearly normal cardiac dimensions in systole and diastole. The absence of improvement of cardiac function, dynamics, and dimensions was observed as expected in the placebo control group.

Thus, the amino acid complex metabolic formulation at a dose of 2 grams 3 times per day for 30 days resulted in an average 24 percent improvement in left ventricular ejection fraction in persons with heart failure due to ischemic heart disease and hypertension, a much greater improvement than would be expected of the sum of the individual amino acid actions at the dosages given.

In addition, there was significant favorable myocardial reshaping with resolution of much of the abnormal ventricular dilation at end-systole and end-diastole. Ventricular and supraventricular arrhythmias were much reduced in the treatment group, whereas both of these worsened significantly in the placebo control group. The dynamics of diastolic function were also much improved in the treatment group whereas this function was unchanged in the placebo control group. A statistically significant near doubling of collagen generation in the treatment group as measured by serial oxyproline levels suggests that myocardial regeneration contributed to the clinical and physiologic improvement.

A laser driven quantum enhancement process is believed to have contributed to the potent synergistic action by reducing the pro-inflammatory tendency of the amino acids thus treated. Of the study group subjects with mild, moderate, or severe heart failure who were treated with the laser enhanced amino acid complex, there was overall improvement to normal or nearly normal cardiac function in 58.8 percent of subjects, compared to no significant improvement in the placebo group.

What is claimed:

1. A blend of amino acids, comprising a plurality of amino acid powders exposed to pulsed laser radiation, the pulsed laser radiation obtained by passing laser radiation through a device comprising a first diffraction grating, a second diffraction grating, and a refractive element positioned between the first and second diffraction gratings, thereby canceling a portion of the laser radiation by destructive interference, and producing pulses of laser radiation by constructive interference.

2. The blend of amino acids according to claim 1, wherein the pulsed laser radiation has a pulse length of no more than $10^{-9}$ seconds.

3. The blend of amino acids according to claim 1, wherein the laser radiation with a laser having a center frequency of about 400 to about 550 nm.

4. The blend of amino acids according to claim 1, wherein the plurality of amino acid powders comprises glycine, DL-phenylalanine, L-glutamic acid, L-lysine, L-glutamine, L-arginine, L-leucine, L-isoleucine, L-valine, L-methionine, L-serine, L-threonine, L-alanine, L-aspartic acid, L-histidine, L-proline, L-ornithine, L-citrulline, L-taurine, and L-cysteine.

5. The blend of amino acids according to claim 1, wherein the plurality of amino acid powders comprises 34.1±3.4 percent by weight glycine, 11.9±1.19 percent by weight DL-phenylalanine, 6.3±0.63 percent by weight L-glutamic acid, 6.3±0.63 percent by weight L-lysine, 6.3±0.63 percent by weight L-glutamine, 5.6±0.56 percent by weight L-arginine, 5.6±0.56 percent by weight L-leucine, 3.7±0.37 percent by weight L-isoleucine, 3.1±0.31 percent by weight L-valine, 3.1±0.31 percent by weight L-methionine, 3.1±0.31 percent by weight L-serine, 2.5±0.25 percent by weight L-threonine, 1.6±0.16 percent by weight L-alanine, 1.3±0.13 percent by weight L-aspartic acid, 1.3±0.13 percent by weight L-histidine, 1.3±0.13 percent by weight L-proline, 1.1±0.011 percent by weight L-ornithine, 0.9±0.09 percent by weight L-citrulline, 0.6±0.06 percent by weight L-taurine, and 0.3±0.03 percent by weight L-cysteine.

6. The blend of amino acids according to claim 1, wherein the plurality of amino acid powders comprises about 34.1 percent by weight glycine, about 11.9 percent by weight DL-phenylalanine, about 6.3 percent by weight L-glutamic acid, about 6.3 percent by weight L-lysine, about 6.3 percent by weight L-glutamine, about 5.6 percent by weight L-arginine, about 5.6 percent by weight L-leucine, about 3.7 percent by weight L-isoleucine, about 3.1 percent by weight L-valine, about 3.1 percent by weight L-methionine, about 3.1 percent by weight L-serine, about 2.5 percent by weight L-threonine, about 1.6 percent by weight L-alanine, about 1.3 percent by weight L-aspartic acid, about 1.3 percent by weight L-histidine, about 1.3 percent by weight L-proline, about 1.1 percent by weight L-ornithine, about 0.9 percent by weight L-citrulline, about 0.6 percent by weight L-taurine, and about 0.3 percent by weight L-cysteine.

7. A process for preparing a laser treated blend of amino acids, comprising:
obtaining a blend of amino acid powders; and
exposing the blend of amino acids to pulsed laser radiation, the pulsed laser radiation obtained by passing laser radiation through a device comprising a first diffraction grating, a second diffraction grating, and a refractive element positioned between the first and second diffraction gratings, thereby canceling a portion of the laser radiation by destructive interference, and producing pulses of laser radiation by constructive interference.

8. The process according to claim 7, wherein the blend of amino acid powders comprises glycine, DL-phenylalanine, L-glutamic acid, L-lysine, L-glutamine, L-arginine, L-leucine, L-isoleucine, L-valine, L-methionine, L-serine, L-threonine, L-alanine, L-aspartic acid, L-histidine, L-proline, L-ornithine, L-citrulline, L-taurine, and L-cysteine.

9. The process according to claim 7, wherein the plurality of amino acid powders comprises 34.1±3.4 percent by weight glycine, 11.9±1.19 percent by weight DL-phenylalanine, 6.3±0.63 percent by weight L-glutamic acid, 6.3±0.63 percent by weight L-lysine, 6.3±0.63 percent by weight L-glutamine, 5.6±0.56 percent by weight L-arginine, 5.6±0.56 percent by weight L-leucine, 3.7±0.37 percent by weight L-isoleucine, 3.1±0.31 percent by weight L-valine, 3.1±0.31 percent by weight L-methionine, 3.1±0.31 percent by weight L-serine, 2.5±0.25 percent by weight L-threonine, 1.6±0.16 percent by weight L-alanine, 1.3±0.13 percent by weight L-aspartic acid, 1.3±0.13 percent by weight L-histidine, 1.3±0.13 percent by weight L-proline, 1.1±0.011 percent by weight L-ornithine, 0.9±0.09 percent by weight L-citrulline, 0.6±0.06 percent by weight L-taurine, and 0.3±0.03 percent by weight L-cysteine.

10. The process according to claim 7, wherein the blend of amino acid powders comprises about 34.1 percent by weight glycine, about 11.9 percent by weight DL-phenylalanine, about 6.3 percent by weight L-glutamic acid, about 6.3 percent by weight L-lysine, about 6.3 percent by weight L-glutamine, about 5.6 percent by weight L-arginine, about 5.6 percent by weight L-leucine, about 3.7 percent by weight L-isoleucine, about 3.1 percent by weight L-valine, about 3.1 percent by weight L-methionine, about 3.1 percent by weight L-serine, about 2.5 percent by weight L-threonine, about 1.6 percent by weight L-alanine, about 1.3 percent by weight L-aspartic acid, about 1.3 percent by weight L-histidine, about 1.3 percent by weight L-proline, about 1.1 percent by weight L-ornithine, about 0.9 percent by weight L-citrulline, about 0.6 percent by weight L-taurine, and about 0.3 percent by weight L-cysteine.

11. The process according to claim 7, wherein the pulsed laser radiation has a pulse length of no more than $10^{-9}$ second.

12. The process according to claim 7, further comprising providing the laser radiation with a laser having a center frequency of about 400 to about 550 nm.

13. A method of regenerating active myocardial tissue, comprising administering a blend of amino acids, comprising a plurality of amino acid powders exposed to pulsed laser radiation to a patient, the pulsed laser radiation obtained by passing laser radiation through a device comprising a first diffraction grating, a second diffraction grating, and a refractive element positioned between the first and second diffraction gratings, thereby canceling a portion of the laser radiation by destructive interference, and producing pulses of laser radiation by constructive interference.

14. The method according to claim 13, wherein the plurality of amino acid powders comprises glycine, DL-phenylalanine, L-glutamic acid, L-lysine, L-glutamine, L-arginine, L-leucine, L-isoleucine, L-valine, L-methionine, L-serine, L-threonine, L-alanine, L-aspartic acid, L-histidine, L-proline, L-ornithine, L-citrulline, L-taurine, and L-cysteine.

15. The method according to claim 13, wherein the plurality of amino acid powders comprises 34.1±3.4 percent by weight glycine, 11.9±1.19 percent by weight DL-phenylalanine, 6.3±0.63 percent by weight L-glutamic acid, 6.3±0.63 percent by weight L-lysine, 6.3±0.63 percent by weight L-glutamine, 5.6±0.56 percent by weight L-arginine, 5.6±0.56 percent by weight L-leucine, 3.7±0.37 percent by weight L-isoleucine, 3.1±0.31 percent by weight L-valine, 3.1±0.31 percent by weight L-methionine, 3.1±0.31 percent by weight L-serine, 2.5±0.25 percent by weight L-threonine, 1.6±0.16 percent by weight L-alanine, 1.3±0.13 percent by weight L-aspartic acid, 1.3±0.13 percent by weight L-histidine, 1.3±0.13 percent by weight L-proline, 1.1±0.011 percent by weight L-ornithine, 0.9±0.09 percent by weight L-citrulline, 0.6±0.06 percent by weight L-taurine, and 0.3±0.03 percent by weight L-cysteine.

16. The method according to claim 13, wherein the plurality of amino acid powders comprises about 34.1 percent by weight glycine, about 11.9 percent by weight DL-phenylalanine, about 6.3 percent by weight L-glutamic acid, about 6.3 percent by weight L-lysine, about 6.3 percent by weight L-glutamine, about 5.6 percent by weight L-arginine, about 5.6 percent by weight L-leucine, about 3.7 percent by weight L-isoleucine, about 3.1 percent by weight L-valine, about 3.1 percent by weight L-methionine, about 3.1 percent by weight L-serine, about 2.5 percent by weight L-threonine, about 1.6 percent by weight L-alanine, about 1.3 percent by weight L-aspartic acid, about 1.3 percent by weight L-histidine, about 1.3 percent by weight L-proline, about 1.1 percent by weight L-ornithine, about 0.9 percent by weight L-citrulline, about 0.6 percent by weight L-taurine, and about 0.3 percent by weight L-cysteine.

17. The method according to claim 13, wherein the pulses of laser radiation have a pulse length of no more than $10^{-9}$ seconds.

18. The method according to claim 13, wherein the laser radiation with a laser having a center frequency of about 400 to about 550 nm.

* * * * *